United States Patent
Yang et al.

(10) Patent No.: US 12,109,073 B2
(45) Date of Patent: Oct. 8, 2024

(54) META FLUORESCENCE TISSUE MIMICKING PHANTOM OF IMAGING METHOD AND SYSTEM

(71) Applicant: ZHEJIANG LAB, Zhejiang (CN)

(72) Inventors: Qing Yang, Hangzhou (CN); Ji Qi, Hangzhou (CN); Xiaopeng Chen, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/398,177

(22) Filed: Dec. 28, 2023

(65) Prior Publication Data
US 2024/0261056 A1 Aug. 8, 2024

(30) Foreign Application Priority Data
Feb. 8, 2023 (CN) .......................... 202310076358.1

(51) Int. Cl.
| | | |
|---|---|---|
| A61B 5/00 | (2006.01) | |
| A61B 1/04 | (2006.01) | |
| A61B 90/00 | (2016.01) | |
| G06T 7/00 | (2017.01) | |

(52) U.S. Cl.
CPC .............. *A61B 90/08* (2016.02); *A61B 1/043* (2013.01); *G06T 7/0012* (2013.01); *G06T 2207/10064* (2013.01); *G06T 2207/30024* (2013.01)

(58) Field of Classification Search
CPC ....... A61B 90/08; A61B 1/043; G06T 7/0012; G06T 2207/10064; G06T 2207/30024
See application file for complete search history.

(56) References Cited

FOREIGN PATENT DOCUMENTS

| | | | |
|---|---|---|---|
| CN | 1912587 | A | 2/2007 |
| CN | 103134784 | A | 6/2013 |
| CN | 103654699 | A | 3/2014 |
| CN | 105606581 | A | 5/2016 |
| CN | 107271418 | A | 10/2017 |
| CN | 108742532 | A | 11/2018 |
| CN | 109814361 | A | 5/2019 |
| CN | 110680284 | A | 1/2020 |

(Continued)

OTHER PUBLICATIONS

First Office Action(CN202310076358.1; Date of Mailing: Mar. 24, 2023.
(Continued)

*Primary Examiner* — Joel F Brutus
(74) *Attorney, Agent, or Firm* — W&G Law Group

(57) ABSTRACT

A meta fluorescence tissue mimicking phantom of imaging method and system. The system includes a fluorescence acquisition module configured to acquire spectral information, contrast information and light intensity information of fluorescence molecules in biological tissue, store the spectral information, the contrast information and the light intensity information in a computer, and transmit the spectral information, the contrast information and the light intensity information to a fluorescence reproduction module through a computer communication port; a fluorescence reproduction module configured to generate a fluorescence tissue mimicking phantom according to the spectral information, the contrast information and the light intensity information; and a meta fluorescence tissue-mimicking phantom imaging module configured to perform imaging on the fluorescence tissue mimicking phantom.

5 Claims, 6 Drawing Sheets

(56) References Cited

FOREIGN PATENT DOCUMENTS

| | | |
|---|---|---|
| CN | 110743019 A | 2/2020 |
| CN | 113409466 A | 9/2021 |
| CN | 113985437 A | 1/2022 |
| KR | 20140068640 A | 6/2014 |
| KR | 20180131092 A | 12/2018 |
| WO | 2008081659 A1 | 7/2008 |
| WO | 2014205738 A1 | 12/2014 |
| WO | 2021053245 A1 | 3/2021 |

OTHER PUBLICATIONS

Notice of Allowance(CN202310076358.1); Date of Mailing: Apr. 12, 2023.
Transmissive-Coaxial-Photoacoustic-Endosc-Opic-Imaging-System-for-Digestive-Tract.
Hollow-Focused-PVDF-Transducer-with-Epoxy-Acoustic-Lens-for-Photoacoustic-Endoscopy.
Contrast-Analysis-and-Imaging-Simulation-of-Fluorescence-Imaging-System.
Three-Dimensional-Reconstruction-for-Fluorescence-Tomography-Using-Cylinder-Phantoms.
Study-on-Multi-spectral-Fluorescence-Confocal-Endomicroscopy-System.

META FLUORESCENCE TISSUE MIMICKING PHANTOM OF IMAGING METHOD AND SYSTEM

CROSS-REFERENCE TO RELATED APPLICATIONS

The present application claims priority to Chinese Patent Application No. 202310076358.1, filed on Feb. 8, 2023, the content of which is incorporated herein by reference in its entirety.

TECHNICAL FIELD

The present disclosure relates to the technical field of medical devices, and in particular, to a meta fluorescence tissue mimicking phantom of imaging method and system.

BACKGROUND

With the development of medical and optical technologies, fluorescence endoscopic imaging plays an increasingly important role in surgical navigation. However, a plurality of factors, such as light source characteristics, optical imaging system design and parameters, image sensor performance and settings, image processing algorithms, concentration and usage environment of a fluorescent agent, tissue structure and optical characteristics, will affect final fluorescent image information, thereby affecting clinical diagnosis. The lack of consistency in data from different devices poses significant challenges to device performance evaluation, clinical quality control, algorithm validation and other tasks. Physical phantom may be used for evaluating the fluorescence imaging performance of an imaging system, but the method is prone to being affected by the stability of the fluorescence molecules. There is currently a lack of effective means for evaluating fluorescence imaging devices. How to fabricate a phantom that may be used for florescence imaging with stable properties, reliable quality, easy mass production, and highly consistent optical properties with a real environment of human tissues, and to perform standardized evaluation and testing on fluorescence imaging system devices, are challenges in a standardization process of fluorescence imaging devices.

In view of this, a meta fluorescence tissue mimicking phantom of imaging method and system is proposed.

SUMMARY

In order to solve the above technical problems, the present disclosure provides a meta fluorescence tissue mimicking phantom of imaging method and system.

Technical solutions adopted by the present disclosure are as follows:

The meta fluorescence tissue mimicking phantom of imaging system includes:

A fluorescence acquisition module configured to acquire spectral information, contrast information and light intensity information of fluorescence molecules in a biological tissue, store the spectral information, the contrast information and the light intensity information in a computer, and transmit the spectral information, the contrast information and the light intensity information to a fluorescence reproduction module through a computer communication port.

A fluorescence reproduction module configured to generate a fluorescence tissue mimicking phantom according to the spectral information, the contrast information and the light intensity information.

A meta fluorescence tissue-mimicking phantom imaging module configured to perform imaging on the fluorescence tissue mimicking phantom.

Further, the fluorescence acquisition module includes:

A spectrometer configured to acquire fluorescence emission spectrum information of the fluorescence molecules.

An optical camera configured to acquire fluorescence image contrast information of the fluorescence molecules.

An optical power meter configured to acquire light intensity information of the fluorescence molecules.

The fluorescence emission spectrum information is the spectral information, the fluorescence image contrast information is the contrast information, and the spectral information, the contrast information and the light intensity information are stored in the computer and are transmitted to the fluorescence reproduction module through the computer communication port.

Further, the fluorescence reproduction module includes:

A laser configured to emit super-continuum spectrum beams, and meanwhile used to regulate optical power of the super-continuum spectrum beams according to the light intensity information, and transmit the super-continuum spectrum beams to a spectrum regulation unit.

The spectrum regulation unit configured to regulate the super-continuum spectrum beams according to the spectral information to obtain regulated spectral beams, and transmit the spectral beams to a contrast regulation unit.

The contrast regulation unit configured to regulate spatial contrast distribution of the spectral beams according to the contrast information to obtain fluorescent beams, and project the fluorescent beams to generate the fluorescence tissue mimicking phantom.

Further, the laser is a super-continuum laser, and the super-continuum spectrum beams contain light with a continuously changing wavelength.

Further, the spectrum regulation unit includes:

A coupling lens configured to perform collimation on the super-continuum spectrum beams to obtain collimated beams, and transmit the collimated beams to the first grating.

A first grating configured to generate dispersion of the collimated beams to obtain unfocused dispersed light, and transmit the unfocused dispersed light to the first focusing lens.

A first focusing lens configured to transform the unfocused dispersed light into focused dispersed light, and transmit the focused dispersed light to a first spatial light modulation device.

The first spatial light modulation device configured to regulate a spectral composition of the focused dispersed light according to the spectral information to make the spectral composition of the focused dispersed light be consistent with the spectral information to obtain regulated focused dispersed light, and transmit the regulated focused dispersed light to a second focusing lens.

The second focusing lens configured to transform the regulated focused dispersed light into regulated unfocused dispersed light, and transmit the regulated unfocused dispersed light to a second grating.

The second grating configured to combine the regulated unfocused dispersed light into a beam of light to obtain a combined beam light, and transmit the combined beam light to a light homogenizer.

The light homogenizer configured to perform uniform light on the combined beam light to obtain regulated spectral beams.

Further, the first spatial light modulation device adopts a meta micromirror device (DMD).

Further, the contrast regulation unit includes:

A second spatial light modulation device, adopting a meta micromirror device (DMD), and configured to regulate spatial contrast distribution of the spectral beams according to the contrast information to make the spatial contrast distribution of the spectral beams be consistent with the contrast information to obtain fluorescent beams.

A projection lens configured to project the fluorescent beams to generate a fluorescence tissue mimicking phantom.

Further, the meta fluorescence tissue-mimicking phantom imaging module includes:

An imaging lens configured to perform imaging on the fluorescence tissue mimicking phantom to obtain an imaging result, and transmit the imaging result to a camera.

The camera configured to transmit the imaging result to the computer, and perform parameter analysis of resolution, sensitivity and/or depth-of-field on the imaging result in the computer.

The present disclosure further provides use of the meta fluorescence tissue mimicking phantom of imaging system in traceability of International System of Units, an optical power meter with a clear aperture of D cm is adopted and placed at a position with a distance of R cm from a meta phantom, then the optical power of the current meta phantom is measured to be E mW, a luminous area $A=\frac{1}{4}*pi*D^2$, a solid angle $theta=A/R^2$, and a phantom radiation quantity is equal to E/A/theta, in $mW/cm^2/sr$.

The present disclosure further provides a meta fluorescence tissue mimicking phantom of imaging method, including the following steps:

Step S1: acquiring, by a fluorescence acquisition module, spectral information, contrast information and light intensity information of fluorescence molecules in biological tissue, storing the spectral information, the contrast information and the light intensity information in a computer, and transmitting the spectral information, the contrast information and the light intensity information to a fluorescence reproduction module through a computer communication port.

Step S2: generating, by the fluorescence reproduction module, a fluorescence meta phantom according to the spectral information, the contrast information and the light intensity information.

Step S3: imaging, by a meta fluorescence tissue-mimicking phantom imaging module, on the fluorescence phantom.

The present disclosure has the beneficial effects.

1. A meta method is used to replace traditional fluorescence molecules fluorescence, and the meta phantom has high stability.
2. It is different from the fluorescence molecules that can only emit fluorescence with specific wavelengths, the meta biomimetic phantom may mimic an emission spectrum of any fluorescence molecule, and has diversity and flexibility.
3. The fluorescent spectrum and light intensity may be adjusted through light intensity regulation, and the meta phantom has extremely high accuracy.
4. The fluorescent meta phantom may be used for evaluating a fluorescence imaging device from multiple degrees, including sensitivity, resolution, depth-of-field and other characteristics, and the meta phantom may be traced back to international units.

REFERENCE SIGNS

1—fluorescence acquisition module, 11—spectrometer, 12—optical camera, 13—optical power meter, 2—fluorescence reproduction module, 21—laser, 22—spectrum regulation unit, 221—coupling lens, 222—first grating, 223—first focusing lens, 224—first spatial light modulation device, 225—second focusing lens, 226—second grating, 227—light homogenizer, 23—contrast regulation unit, 231—second spatial light modulation device, 232—projection lens, 3—meta fluorescence tissue-mimicking phantom imaging module, 31—imaging lens, and 32—camera.

DESCRIPTION OF EMBODIMENTS

The following description of at least one exemplary embodiment is actually only illustrative and does not serve as any limitation to the present disclosure, and application or use thereof. Based on the embodiments in the present disclosure, all other embodiments obtained by those ordinarily skilled in the art without creative labor fall within the scope of protection of the present disclosure.

Figure 1:
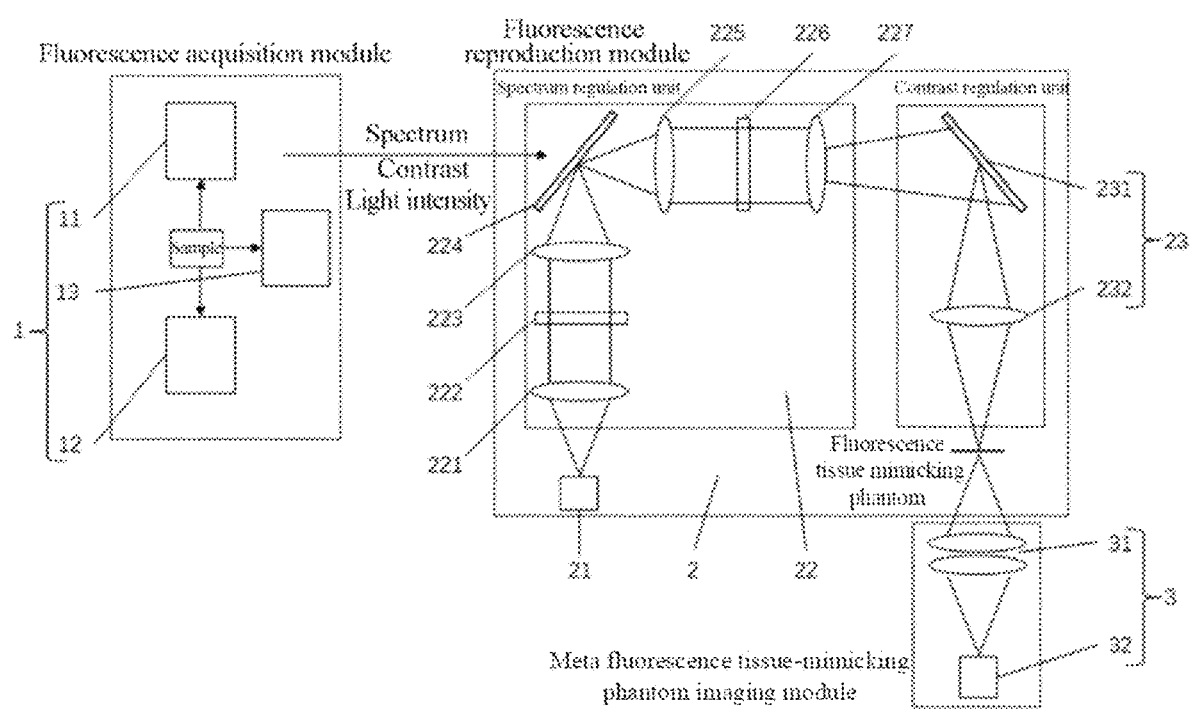
FIG. 1 is a schematic structural diagram of a meta fluorescence tissue-mimicking phantom of imaging system in the present disclosure.

Referring to FIG. 1, a meta fluorescence tissue mimicking phantom of imaging system includes:

The fluorescence acquisition module 1 is configured to acquire spectral information, contrast information and light intensity information of fluorescence molecules in biological tissue, store the spectral information, the contrast information and the light intensity information in a computer, and transmit the spectral information, the contrast information and the light intensity information to a fluorescence reproduction module 2 through a computer communication port.

The fluorescence acquisition module 1 includes:

The spectrometer 11 is configured to acquire fluorescence emission spectrum information of the fluorescence molecules in the biological tissue.

The optical camera 12 is configured to acquire fluorescence image contrast information of the fluorescence molecules in the biological tissue.

The optical power meter 13 is configured to acquire light intensity information of the fluorescence molecules in the biological tissue.

The fluorescence emission spectrum information is the spectral information, the fluorescence image contrast information is the contrast information, and the spectral information, the contrast information and the light intensity information are stored in the computer and are transmitted to the fluorescence reproduction module 2 through the computer communication port.

The fluorescence reproduction module 2 is configured to generate a fluorescence tissue mimicking phantom according to the spectral information, the contrast information and the light intensity information.

The fluorescence reproduction module 2 includes:

The laser 21 is configured to emit super-continuum spectrum beams, and meanwhile is configured to regulate optical power of the super-continuum spectrum beams according to the light intensity information, and transmit the super-continuum spectrum beams to the spectrum regulation unit 22.

The laser 21 is the super-continuum laser, and the super-continuum spectrum beams contain light with the continuously changing wavelength.

The spectrum regulation unit 22 is configured to regulate the super-continuum spectrum beams according to the spectral information to obtain regulated spectral beams, and transmit the spectral beams to a contrast regulation unit 23.

The spectrum regulation unit 22 includes:

The coupling lens 221 is configured to perform collimation on the super-continuum spectrum beams to obtain collimated beams, and transmit the collimated beams to a first grating 222.

The first grating 222 is configured to generate dispersion of the collimated beams to obtain unfocused dispersed light, and transmit the unfocused dispersed light to a first focusing lens 223.

The first focusing lens 223 is configured to transform the unfocused dispersed light into focused dispersed light, and transmit the focused dispersed light to the first spatial light modulation device 224.

The first spatial light modulation device 224 is configured to regulate the spectral composition of the focused dispersed light according to the spectral information to make the spectral composition of the focused dispersed light be consistent with the spectral information to obtain regulated focused dispersed light, and transmit the regulated focused dispersed light to the second focusing lens 225.

The first spatial light modulation device 224 adopts the meta micromirror device (DMD).

The second focusing lens 225 is configured to transform the regulated focused dispersed light into regulated unfocused dispersed light, and transmit the regulated unfocused dispersed light to the second grating 226.

The second grating 226 is configured to combine the regulated unfocused dispersed light into the beam of light to obtain the combined beam light, and transmit the combined beam light to the light homogenizer 227.

The light homogenizer 227 is configured to perform uniform light on the combined beam light to obtain the regulated spectral beams.

The contrast regulation unit 23 is configured to regulate spatial contrast distribution of the spectral beams according to the contrast information to obtain fluorescent beams, and project the fluorescent beams to generate the fluorescence tissue mimicking phantom.

The contrast regulation unit 23 includes:

The second spatial light modulation device 231, adopting the meta micromirror device (DMD), and used to regulate spatial contrast distribution of the spectral beams according to the contrast information to make the spatial contrast distribution of the spectral beams be consistent with the contrast information to obtain fluorescent beams.

The projection lens 232 is configured to project the fluorescent beams to generate a fluorescence tissue mimicking phantom.

The meta fluorescence tissue-mimicking phantom imaging module 3 is configured to perform imaging on the fluorescence tissue mimicking phantom.

The meta fluorescence tissue-mimicking phantom imaging module 3 includes:

The imaging lens 31 is configured to perform imaging on the fluorescence tissue mimicking phantom to obtain the imaging result, and transmit the imaging result to the camera 32.

The camera 32 is configured to transmit the imaging result to the computer, and perform parameter analysis of resolution, sensitivity and/or depth-of-field on the imaging result in the computer.

Figure 2:
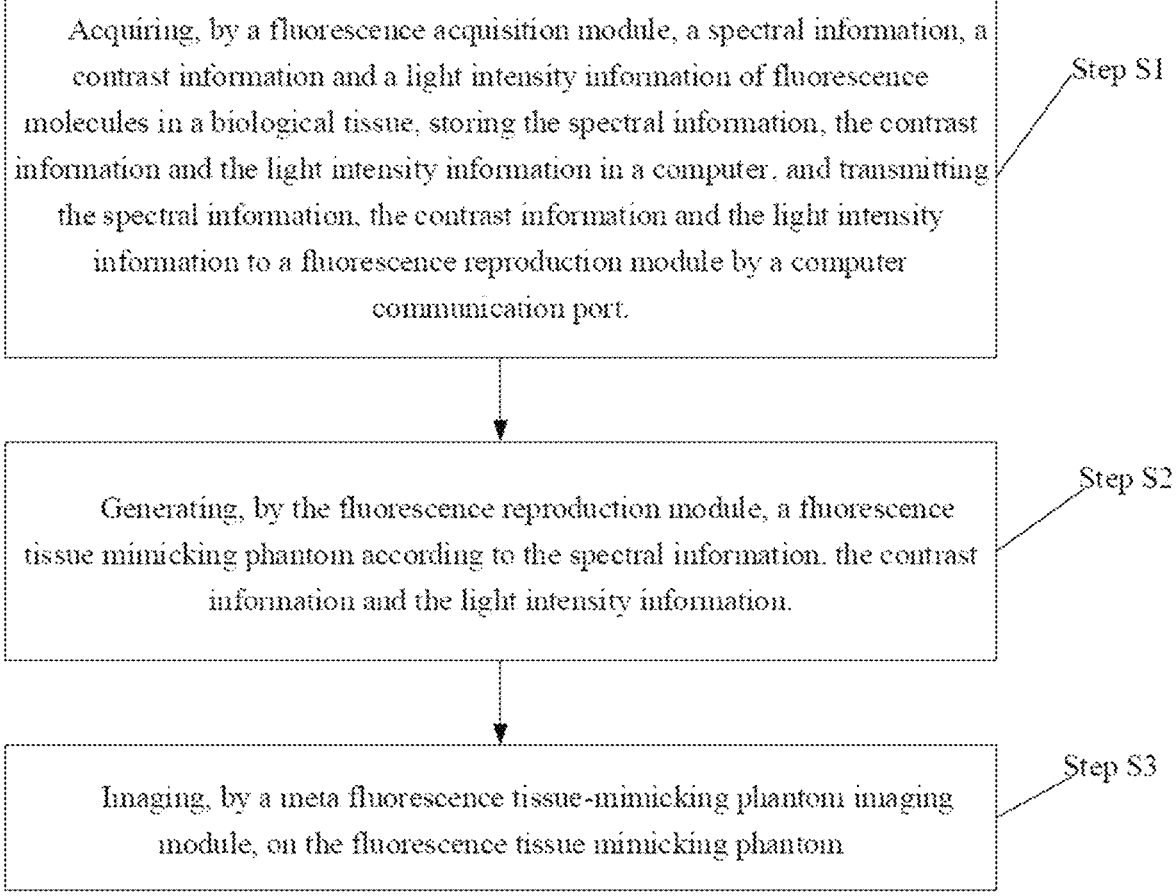
FIG. 2 is a schematic flowchart of a meta fluorescence tissue-mimicking phantom imaging method in the present disclosure.

Referring to FIG. 2, the meta fluorescence tissue mimicking phantom of imaging method includes the following steps:

Step S1: the fluorescence acquisition module acquires spectral information, contrast information and light intensity information of fluorescence molecules in biological tissue, stores the spectral information, the contrast information and the light intensity information in a computer, and transmits the spectral information, the contrast information and the light intensity information to a fluorescence reproduction module through a computer communication port.

Step S2: the fluorescence reproduction module generates the fluorescence tissue mimicking phantom according to the spectral information, the contrast information and the light intensity information.

Step S3: the meta fluorescence tissue-mimicking phantom imaging module performs imaging on the fluorescence tissue mimicking phantom.

Embodiment:

The meta fluorescence tissue mimicking phantom of imaging system includes:

The fluorescence acquisition module 1 is configured to acquire spectral information, contrast information and light intensity information of fluorescence molecules in biological tissue, store the spectral information, the contrast information and the light intensity information in the computer, and transmit the spectral information, the contrast information and the light intensity information to the fluorescence reproduction module 2 through the computer communication port.

The fluorescence acquisition module 1 includes:

The spectrometer 11 is configured to acquire fluorescence emission spectrum information of the fluorescence molecules in the biological tissue.

The optical camera 12 is configured to acquire fluorescence image contrast information of the fluorescence molecules in the biological tissue.

The optical power meter 13 is configured to acquire light intensity information of the fluorescence molecules in the biological tissue.

The fluorescence emission spectrum information is the spectral information, the fluorescence image contrast information is the contrast information, and the spectral information, the contrast information and the light intensity information are stored in the computer and are transmitted to the fluorescence reproduction module 2 through the computer communication port.

Fluorescence molecule samples are diluted in water and placed in a 4.5 ml cuvette for detection; a narrowband light source is adopted to excite the fluorescent samples, and fluorescent signals generated by the samples are detected by the spectrometer 11, and meanwhile are detected by the optical camera 12, which may obtain spectral information and light intensity information of the fluorescence molecules in the biological tissue. Taking indocyanine green (ICG), a commonly used near infrared fluorescence dye in clinical practice, as an example, 1 mg of ICG powder is dissolved in 1 ml of distilled water, then 0.01 ml of a mixed solution is taken, 1 ml of distilled water is added into it, a final solution concentration is 0.01 mg/ml, and a fluorescent phenomenon of ICG is relatively obvious. A mixed ICG solution is placed in the cuvette, a 780 nm LED beam is irradiated through a top end of a container to perform fluorescence excitation on ICG molecules in the solution; on a side face of the container, the fluorescent signals are collected through a lens and focused on an end face of optical fibers, and the fluorescent signals are transmitted into the spectrometer 11 through the optical fibers to obtain fluorescence emission spectrum information; on the other side face of the container, the fluorescent signals are collected by the optical camera 12 through an imaging lens to obtain fluorescence image contrast information; and the optical power meter 13 is placed on a third side face of the container to measure light intensity information of the fluorescent signals for traceability of International System of Units for tissue mimicking phantoms. In a process of spectral measurement, excitation light may have a significant impact on a fluorescence emission spectrum, a spectral curve of an excitation light source may be measured separately, and the spectral curve of the light source is subtracted from an ICG measured spectral curve to eliminate the impact.

The fluorescence reproduction module 2 used to generate the fluorescence tissue mimicking phantom according to the spectral information, the contrast information and the light intensity information.

The fluorescence reproduction module 2 includes:

The laser 21 is configured to emit super-continuum spectrum beams, and meanwhile is configured to regulate optical power of the super-continuum spectrum beams according to the light intensity information, and transmit the super-continuum spectrum beams to the spectrum regulation unit 22.

The laser 21 is the super-continuum laser, and the super-continuum spectrum beams contain light with the continuously changing wavelength.

The spectrum regulation unit 22 is configured to regulate the super-continuum spectrum beams according to the spectral information to obtain regulated spectral beams, and transmit the spectral beams to a contrast regulation unit 23.

The spectrum regulation unit 22 includes:

The coupling lens 221 is configured to perform collimation on the super-continuum spectrum beams to obtain the collimated beams, and transmit the collimated beams to a first grating 222.

The first grating 222 is configured to generate dispersion of the collimated beams to obtain unfocused dispersed light, and transmit the unfocused dispersed light to the first focusing lens 223.

The first focusing lens 223 is configured to transform the unfocused dispersed light into focused dispersed light, and transmit the focused dispersed light to the first spatial light modulation device 224.

The first spatial light modulation device 224 is configured to regulate a spectral composition of the focused dispersed light according to the spectral information to make the spectral composition of the focused dispersed light be consistent with the spectral information to obtain regulated focused dispersed light, and transmit the regulated focused dispersed light to a second focusing lens 225.

The first spatial light modulation device 224 adopts a meta micromirror device (DMD).

The second focusing lens 225 is configured to transform the regulated focused dispersed light into regulated unfocused dispersed light, and transmit the regulated unfocused dispersed light to the second grating 226.

The second grating 226 is configured to combine the regulated unfocused dispersed light into a beam of light to obtain the combined beam light, and transmit the combined beam light to the light homogenizer 227.

The light homogenizer 227 is configured to perform uniform light on the combined beam light to obtain regulated spectral beams.

The laser 21 with a broadband light source is adopted as a luminescent source, such as a super-continuum laser. Since a wavelength range of the super-continuum laser may reach 200-2000 nm, the luminescence of any fluorescence molecule within this range may be simulated. Total power of the light source is 20 W, and a power density may be calculated to be approximately 11 mW/nm. The light source is collimated through the coupling lens 221 to output collimated beams, the beams with a diameter of 8 mm may be suitable for matching with a chip size (0.95 inches) of the first spatial light modulation device (DMD) 224, dispersion is generated by the first grating (600 line pairs/millimeter) to obtain unfocused dispersed light, so that different colors of light is irradiated to different regions of the first spatial light modulation device (DMD) 224, and spectral modulation of the beams is achieved through light field regulation. In an embodiment, each column of pixels on the first spatial light modulation device (DMD) 224 corresponds to one wavelength of light waves, by controlling the number of pixels opened in this column, the content of the light waves at this wavelength may be controlled; and then, the unfocused dispersed light is combined into one beam through the second grating 226, and then homogenized through the light homogenizer 227 to obtain the regulated spectral beams.

The contrast regulation unit 23 is configured to regulate spatial contrast distribution of the spectral beams according to the contrast information to obtain fluorescent beams, and project the fluorescent beams to generate the fluorescence tissue mimicking phantom.

The contrast regulation unit 23 includes:

The second spatial light modulation device 231, adopting the meta micromirror device (DMD), and used to regulate spatial contrast distribution of the spectral beams according to the contrast information to make the spatial contrast distribution of the spectral beams be consistent with the contrast information to obtain fluorescent beams.

The projection lens 232 is configured to project the fluorescent beams to generate the fluorescence tissue mimicking phantom.

The regulated spectral beams are subjected to light field intensity modulation through the second spatial light modulation device (DMD) 231, and finally are output through the projection lens 232 to form the fluorescence tissue mimicking phantom. According to different imaging requirements, by replacing the projection lens 232, it is easy to adjust the size of the meta fluorescence tissue mimicking phantom.

The meta fluorescence tissue-mimicking phantom imaging module 3 is configured to perform imaging on the fluorescence tissue mimicking phantom.

The meta fluorescence tissue-mimicking phantom imaging module 3 includes:

The imaging lens 31 is configured to perform imaging on the fluorescence tissue mimicking phantom to obtain the imaging result, and transmit the imaging result to a camera 32.

The camera 32 is configured to transmit the imaging result to the computer, and perform parameter analysis of resolution, sensitivity and/or depth-of-field on the imaging result in the computer.

Figure 3:
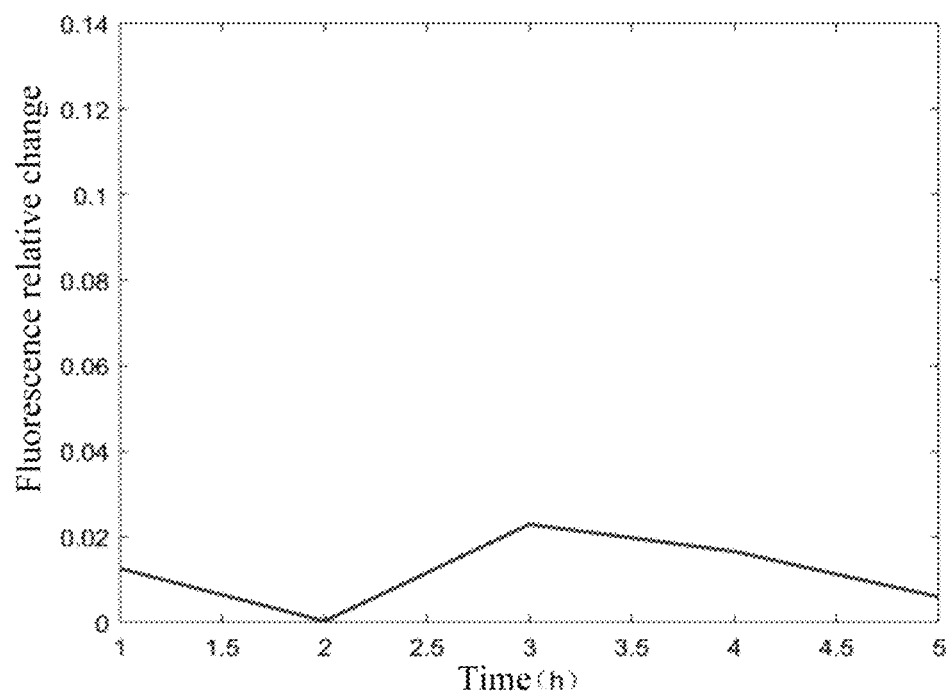
FIG. 3 is a representation diagram of stability of a meta fluorescence tissue-mimicking phantom imaging method in Embodiment 1 of the present disclosure.

Referring to FIG. 3, which is a representation diagram of stability of the tissue mimicking phantom of the meta fluorescence tissue mimicking phantom of imaging method in Embodiment 1 of the present disclosure, within 5 consecutive hours, a fluorescence changing rate of the tissue mimicking phantom is less than 2%, the stability is high, and long-term usage is achieved.

Figure 4:
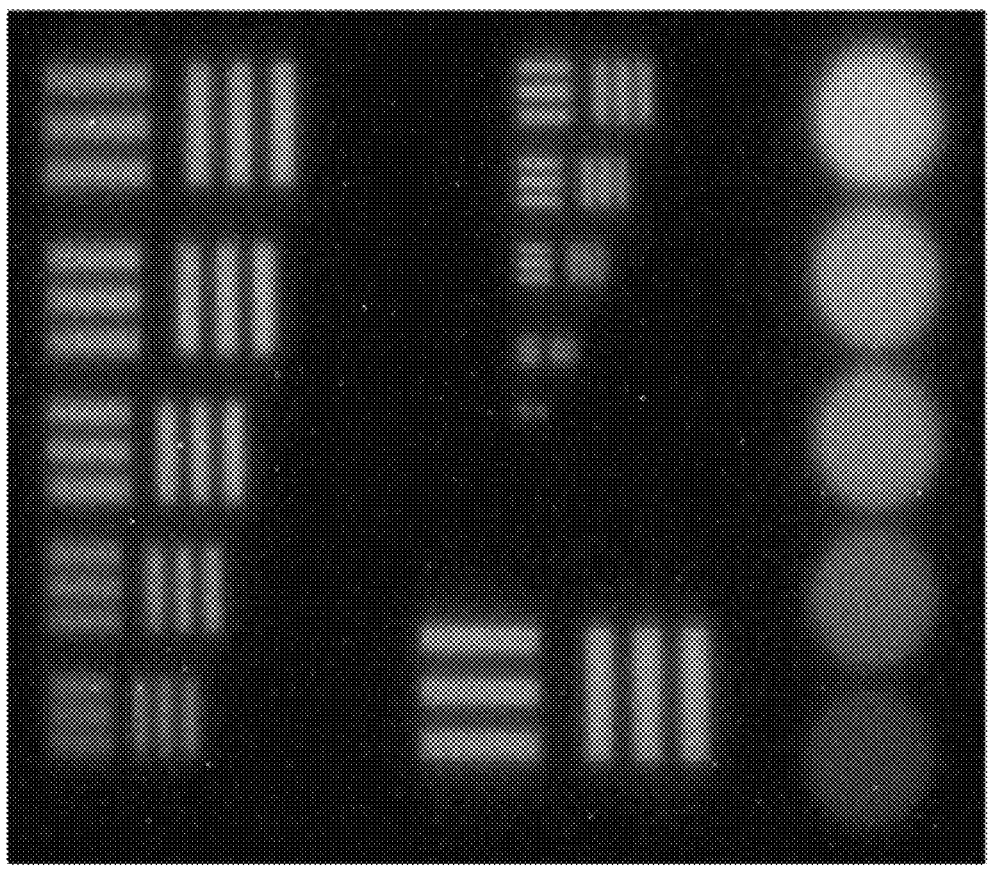
FIG. 4 is a standard model diagram generated by a meta fluorescence tissue-mimicking phantom imaging method in Embodiment 1 of the present disclosure.

Referring to FIG. 4, which is a standard model diagram generated by the meta fluorescence tissue mimicking phantom of imaging method in Embodiment 1 of the present disclosure, it includes two parts, one is resolution line pair, and a resolution range is 0.14-0.51 mm; and in addition, it further includes 5 circular regions with decreasing intensity for sensitivity judgment.

Figure 5:
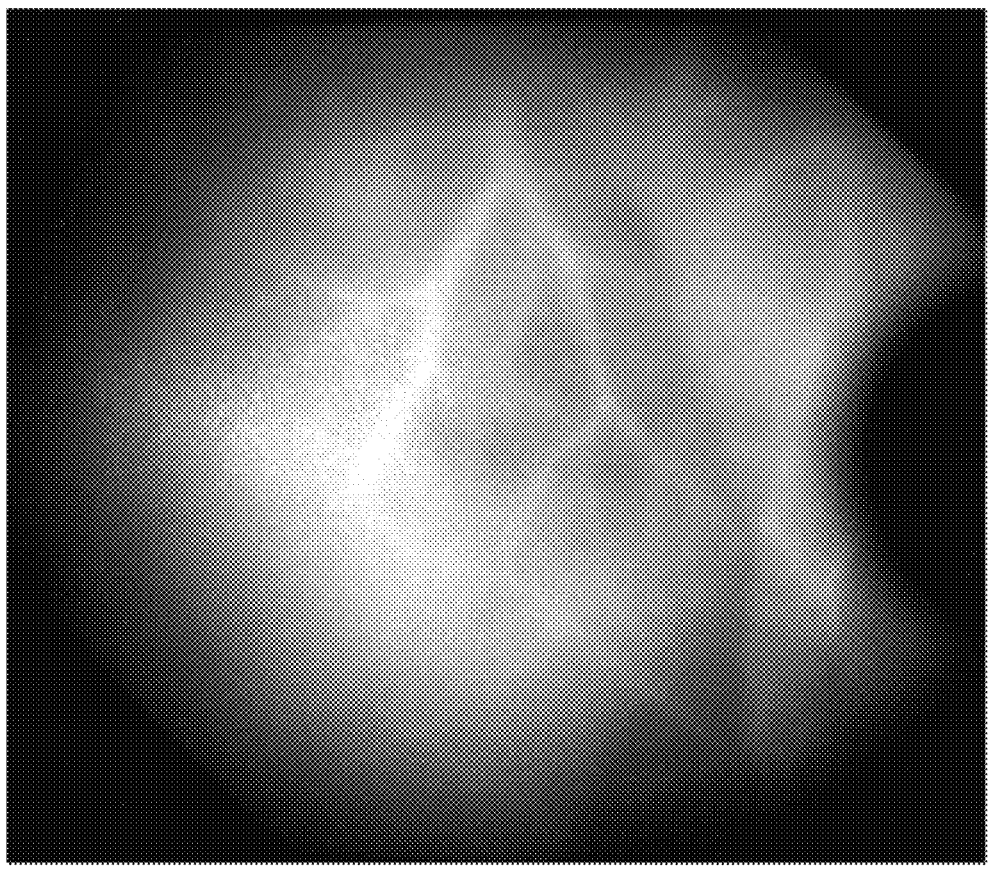
FIG. 5 is a tissue model diagram generated by a meta fluorescence tissue-mimicking phantom imaging method in Embodiment 1 of the present disclosure.

Referring to FIG. 5, it is a tissue model diagram generated by the meta fluorescence tissue mimicking phantom of imaging method in Embodiment 1 of the present disclosure. The tissue mimicking phantom is the ICG fluorescence of surface blood vessels of mammalian abdomen, which is an image captured by the meta fluorescence tissue-mimicking phantom imaging module 3.

Figure 6:
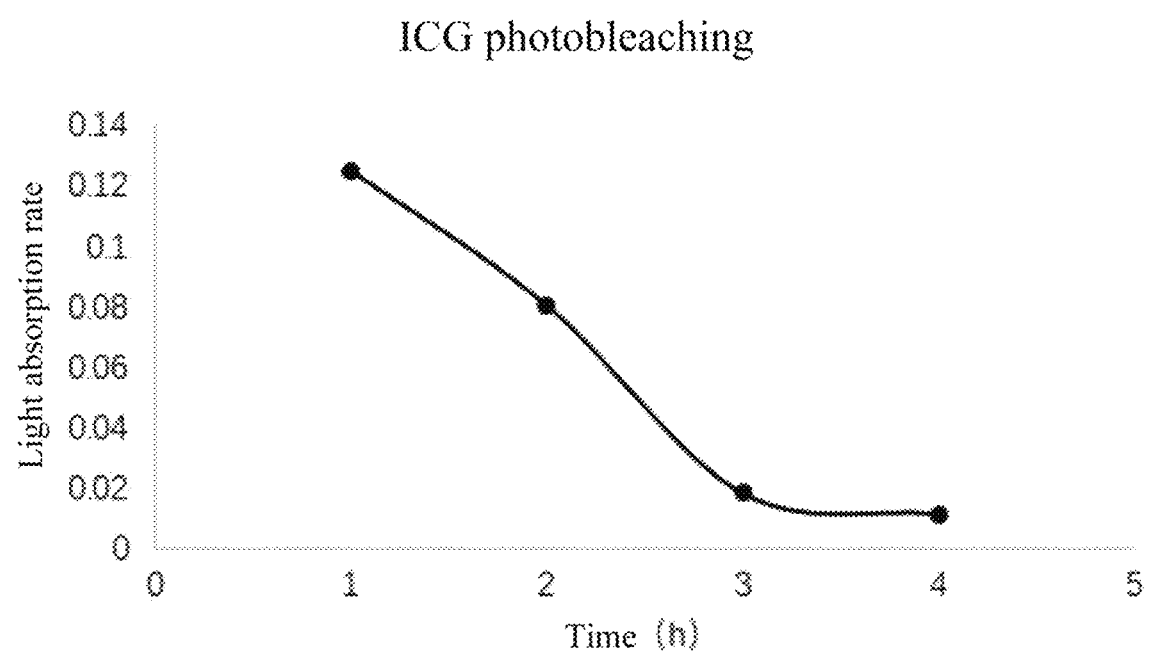
FIG. 6 is an instability degree curve of traditional ICG fluorescence molecules.

Referring to FIG. 6, it is an instability degree curve of traditional ICG fluorescence molecules. From the first to third hour, under continuous light illumination, an ICG absorption rate linearly decreases; and from the third to fourth hour, light irradiation is stopped, and the ICG absorption rate remains unchanged. It indicates that the fluorescence molecules are relatively stable in the absence of light irradiation, while the fluorescence molecules are unstable in the presence of light irradiation.

Taking a fluorescence laparoscope as an example, the laparoscope is placed at a distance of 5-10 cm from the tissue mimicking phantom, an optical clip with a lens is connected to an eye lens of the laparoscope, an optical filter is placed in the clip, then a CMOS camera is connected to the clip, a computer is connected, and the image of the meta tissue mimicking phantom may be displayed on a screen. This module may replace lenses, including objective lenses and the like, according to different application scenarios.

The present disclosure relates to a meta tissue mimicking phantom of imaging system. The platform includes the fluorescence acquisition module 1, the fluorescence reproduction module 2 and the meta fluorescence tissue-mimicking phantom imaging module 3. The fluorescence acquisition module 1 is used to establish a database of emission spectra, light intensity, and contrast information of the fluorescence molecules in a specific environment, as well as to detect spectral, light intensity, and contrast information of the meta tissue mimicking phantom; the fluorescence reproduction module 2 includes two functions: spectral regulation and contrast regulation; and the meta fluorescence tissue-mimicking phantom imaging module 3 may perform imaging on the tissue mimicking phantom. The communication between the fluorescence acquisition module 1 and the fluorescence reproduction module 2 is completed through the computer, and optical information, namely fluorescent signals, is transmitted between the fluorescence reproduction module 2 and the meta fluorescence tissue-mimicking phantom imaging module 3.

The present disclosure relates to the method for evaluating the fluorescence imaging device. Through the fluorescence reproduction module 2, various images may be projected, including stripe pairs with different densities, circular light spots with varying intensities, and other more complex shapes. The fluorescence imaging system performs imaging on the fluorescent tissue mimicking phantom of, and the various imaging performance of the fluorescence imaging system may be determined according to an imaging result.

The present disclosure relates to use of the meta fluorescence biomimetic tissue mimicking phantom of imaging system in traceability of International System of Units for tissue mimicking phantoms, the optical power meter with a clear aperture of D cm is adopted and placed at the position with the distance of R cm from the tissue mimicking phantom, then an optical power of the current tissue mimicking phantom is measured to be E mW, a luminous area $A=\frac{1}{4}*pi*D^2$, a solid angle $theta=A/R^2$, and a phantom radiation quantity is equal to $E/A/theta$, with a unit of $mW/cm^2/sr$.

The foregoing descriptions are only preferred embodiments of the present disclosure and are not used to limit the present disclosure. For those skilled in the art, the present disclosure can have various modifications and changes. Any modification, equivalent replacement, improvement, etc. made within the spirit and principle of the present disclosure should be included in the protection scope of the present disclosure.

What is claimed is:

1. A meta fluorescence tissue mimicking phantom of imaging system, comprising:

a fluorescence acquisition module configured to acquire a spectral information, a contrast information and a light intensity information of fluorescence molecules in a biological tissue, store the spectral information, the contrast information and the light intensity information in a computer, and transmit the spectral information, the contrast information and the light intensity information to a fluorescence reproduction module by a computer communication port;

the fluorescence reproduction module configured to generate a fluorescence tissue mimicking phantom according to the spectral information, the contrast information and the light intensity information; and a meta fluorescence tissue-mimicking phantom imaging module configured to perform imaging on the fluorescence tissue mimicking phantom;

wherein the fluorescence reproduction module comprises:

a laser configured to emit super-continuum spectrum beams, regulate an optical power of the super-continuum spectrum beams according to the light intensity information, and transmit the super-continuum spectrum beams to a spectrum regulation unit;

the spectrum regulation unit configured to regulate the super-continuum spectrum beams according to the spectral information to obtain regulated spectral beams, and transmit the regulated spectral beams to a contrast regulation unit; and the contrast regulation unit configured to regulate a spatial contrast distribution of the regulated spectral beams according to the contrast information to obtain fluorescent beams, and project the fluorescent beams to generate the fluorescence tissue mimicking phantom;

wherein the laser comprises a super-continuum laser, and the super-continuum spectrum beams comprise lights with a continuously changing wavelength;

wherein the spectrum regulation unit comprises:
a coupling lens configured to collimate on the supercontinuum spectrum beams to obtain collimated beams, and transmit the collimated beams to a first grating;
the first grating configured to generate dispersion of the collimated beams to obtain a unfocused dispersed light, and transmit the unfocused dispersed light to a first focusing lens;
the first focusing lens configured to transform the unfocused dispersed light into a focused dispersed light, and transmit the focused dispersed light to a first spatial light modulation device;
the first spatial light modulation device configured to regulate a spectral composition of the focused dispersed light according to the spectral information to allow the spectral composition of the focused dispersed light be consistent with the spectral information to obtain regulated focused dispersed light, and transmit the regulated focused dispersed light to a second focusing lens; wherein the first spatial light modulation device adopts a meta micromirror device (DMD);
the second focusing lens configured to transform the regulated focused dispersed light into regulated unfocused dispersed light, and transmit the regulated unfocused dispersed light to a second grating;
the second grating configured to combine the regulated unfocused dispersed light into a beam of light to obtain a combined beam light, and transmit the combined beam light to a light homogenizer; and
the light homogenizer configured to dodge on the combined beam light to obtain the regulated spectral beams; and
wherein the contrast regulation unit comprises:
a second spatial light modulation device configured to adopt the meta micromirror device (DMD) and regulates the spatial contrast distribution of the regulated spectral beams according to the contrast information to allow the spatial contrast distribution of the regulated spectral beams be consistent with the contrast information to obtain the fluorescent beams; and
a projection lens configured to project the fluorescent beams to generate the fluorescence tissue mimicking phantom.

2. The meta fluorescence tissue mimicking phantom of imaging system according to claim 1, wherein the fluorescence acquisition module comprises:
a spectrometer configured to acquire a fluorescence emission spectrum information of the fluorescence molecules in the biological tissue;
an optical camera configured to acquire a fluorescence image contrast information of the fluorescence molecules in the biological tissue; and
an optical power meter configured to acquire the light intensity information of the fluorescence molecules in the biological tissue; and
wherein the fluorescence emission spectrum information is the spectral information, the fluorescence image contrast information is the contrast information, and the spectral information, the contrast information and the light intensity information are stored in the computer and transmitted to the fluorescence reproduction module by the computer communication port.

3. The meta fluorescence tissue mimicking phantom of imaging system according to claim 1, wherein the meta fluorescence tissue-mimicking phantom imaging module comprises:
an imaging lens configured to perform imaging on the fluorescence tissue mimicking phantom to obtain an imaging result, and transmit the imaging result to a camera; and
the camera configured to transmit the imaging result to the computer, and analyze parameters of resolution, sensitivity and/or depth-of-field on the imaging result in the computer.

4. Use of the meta fluorescence tissue mimicking phantom of imaging system according to claim 1 in traceability of International System of Units for tissue mimicking phantoms, wherein an optical power meter with a clear aperture of D cm is adopted and placed at a position with a distance of R cm from a tissue mimicking phantom, an optical power of the current tissue mimicking phantom is measured to be E mW, a luminous area (A) is calculated by $A=\frac{1}{4}*pi*D^2$, a solid angle (theta) is calculated by $theta-A/R^2$, and a phantom radiation quantity is calculated by E/A/theta, in $mW/cm^2/sr$.

5. A meta fluorescence tissue mimicking phantom of imaging method adopting the system according to claim 1, comprising:
step S1: acquiring, by a fluorescence acquisition module, a spectral information, a contrast information and a light intensity information of fluorescence molecules in a biological tissue, storing the spectral information, the contrast information and the light intensity information in a computer, and transmitting the spectral information, the contrast information and the light intensity information to a fluorescence reproduction module by a computer communication port;
step S2: generating, by the fluorescence reproduction module, a fluorescence tissue mimicking phantom according to the spectral information, the contrast information and the light intensity information; and
step S3: imaging, by a meta fluorescence tissue-mimicking phantom imaging module, on the fluorescence tissue mimicking phantom.

* * * * *